(12) United States Patent
Suzuki

(10) Patent No.: US 7,287,854 B2
(45) Date of Patent: Oct. 30, 2007

(54) OPHTHALMIC PHOTOGRAPHY APPARATUS

(75) Inventor: Takayoshi Suzuki, Gamagori (JP)

(73) Assignee: Kowa Company Ltd. (JP)

( * ) Notice: Subject to any disclaimer, the term of this patent is extended or adjusted under 35 U.S.C. 154(b) by 204 days.

(21) Appl. No.: 11/230,900

(22) Filed: Sep. 20, 2005

(65) Prior Publication Data

US 2006/0082726 A1    Apr. 20, 2006

(30) Foreign Application Priority Data

Sep. 27, 2004  (JP)  ............................. 2004-279554
May 16, 2005  (JP)  ............................. 2005-142033

(51) Int. Cl.
    *A61B 3/14* (2006.01)
(52) U.S. Cl. ..................................... 351/206
(58) Field of Classification Search ............... 351/206, 351/205, 207, 209, 210, 213, 200; 359/350, 359/353, 355–357
    See application file for complete search history.

(56) References Cited

U.S. PATENT DOCUMENTS

2005/0018135 A1*  1/2005  Maeda et al. ............... 351/206

* cited by examiner

*Primary Examiner*—Hung Dang
*Assistant Examiner*—Tuyen Tra
(74) *Attorney, Agent, or Firm*—Adams & Wilks

(57) ABSTRACT

A photographic stop with two apertures is disposed at a position substantially conjugate to the anterior ocular segment of the eye being examined and at a position on the object-side focal surface of an image-forming lens. An eye fundus image is guided via a lattice barrier disposed on the image-side focal surface of the image-forming lens to an imaging CCD. The photographic stop, image-forming lens, lattice barrier and CCD are moved as a unit for focus adjustment. With such a configuration, the photographic stop is always positioned upon the object-side focal surface of the image-forming lens with the optical system kept telecentric even when the focus is adjusted to compensate for differences in diopter of the eye. This eliminates the phenomenon of a stereoscopic view that becomes more concave or convex the nearer to the periphery of the screen and provides good images of the fundus for stereoscopic viewing without any crosstalk of the left and right fundus images upon the image pickup surface.

12 Claims, 12 Drawing Sheets

OPHTHALMIC PHOTOGRAPHY APPARATUS

BACKGROUND OF THE INVENTION

1. Field of the Invention

The present invention relates to an ophthalmic photography apparatus, and more particularly to an ophthalmic photography apparatus that can simultaneously photograph both the left and right images required for stereoscopic viewing of the fundus of an eye being examined.

2. Description of the Prior Art

With a conventional simultaneous stereoscopic fundus camera, as disclosed in Japanese Patent No. 2,642,417 and Japanese Patent No. 2,933,995, a two-aperture stop with two apertures (left and right) is provided at a position conjugate to the anterior ocular segment (conjugate to the pupil) of the eye being examined with respect to the objective lens, and each of the light beams from the fundus that pass through the two apertures is divided by a prism or the like into two optical paths, which are guided to a left-and-right pair of image-forming optical systems where separate images are formed in left and right regions of a film surface or the imaging surface of an imaging device, and then photographed.

In addition, Japanese Patent No. 3,255,730 discloses a configuration wherein the two apertures in the pupil-conjugate two-aperture stop are in the shape of a lengthwise rectangle, while Japanese Laid Open Patent Publication No. 1998-165372 describes a configuration wherein a cylindrical lens is used to cause images of the fundus to be alternately incident upon the pixels of the imaging device and thus photographed. Japanese Laid Open Patent Publication No. 1999-299739 further describes a configuration whereby the aperture stops at the fundus-conjugate position and the pupil-conjugate position are made variable, thereby permitting both stereoscopic and monocular photography to be performed with a single imaging medium.

Moreover, Japanese Laid Open Patent Publication Nos. 1997-18896 and 1997-211388 describe a configuration whereby alternating pixels of the imaging device are guided via a prism or the like to the left or right eye, respectively, thereby allowing the image to be viewed stereoscopically.

In addition, from Japanese Laid Open Patent Publication No. 2004-208744 is known an ophthalmic photography apparatus wherein the photographic stop that eliminates light reflected from the anterior ocular segment of the eye is moved in concert with the focusing lens while maintaining a position substantially conjugate to the anterior ocular segment of the eye being examined.

However, with the conventional configuration as disclosed in any of Japanese Patent Nos. 2,642,417, 2,933,995 or 3,255,730, it is necessary to dispose lenses for each of the left-and-right pair of image-forming optical systems separately for the two optical paths, making the configuration complex and causing the apparatus to become large and also more costly, and moreover there are problems in that the adjustment of the optics of the left and right optical paths becomes exceedingly complex and time-consuming.

In addition, with the configuration disclosed in Japanese Laid Open Patent Publication No. 1998-165372, the two images from the two-aperture stop (the left image and the right image) are alternately incident upon the pixels of the imaging device, but there are problems in that both the left image and the right image are incident upon a single pixel in the periphery of the imaging surface, and thus a good stereoscopic view is not obtained, for example.

In addition, in stereoscopic photography of the eye fundus, the difference of diopter of the eye being examined must be taken into consideration, so if the focusing lens is moved from the reference position to compensate for the difference in diopter of the eye being examined, there are problems in that the conjugate relationship between the position of the anterior ocular segment and the two-aperture stop is upset and also the light passing through the respective apertures of the two-aperture stop is no longer guided to the pixels of the imaging device in a regular manner.

Moreover, even if a two-aperture stop is disposed upon the image-side focal surface of the focusing lens and upon the object-side focal surface of the imaging lens to thereby constitute an image-side telecentric optical system, the system is indeed image-side telecentric for the normal diopter (zero diopter) with an accurate stereoscopic view guaranteed, but if the diopter shifts toward the plus side or the minus side, there is a problem wherein the optical system cannot be kept telecentric during focus adjustment, resulting in a stereoscopic view that becomes more concave or convex the nearer to the periphery of the imaging surface.

SUMMARY OF THE INVENTION

The present invention thus has as its object to solve the problems described above and to provide an ophthalmic photography apparatus that has a simple structure so as to achieve a compact and low-cost apparatus, that allows the optics to be easily adjusted and also that can perform high-quality simultaneous stereoscopic photography of the eye fundus.

According to the invention, an ophthalmic photography apparatus includes an optical system for forming an image of the fundus of an eye being examined, and image pickup means that has a plurality of pixels in a matrix array disposed at the position where the image of the eye fundus is formed by the optical system. The ophthalmic photography apparatus comprises a lens movable within the optical system along the optical axis for compensation for shifts in the image-formation position due to differences in diopter of the eye being examined; a stop with two apertures provided at a position substantially conjugate to the anterior ocular segment of the eye being examined; and a deflecting optical element provided near the imaging surface of the image pickup means; wherein the exit pupil position of the optical system is set to be at infinity, and the image pickup means and the deflecting optical element are disposed such that the light that is incident upon one pixel column of the image pickup means via the optical deflecting element is only that light that passed through one of the two apertures of the stop and light from both apertures is incident upon alternate pixel columns of the image pickup means.

The invention further provides an ophthalmic photography apparatus that includes a first optical system for forming an image of the fundus of an eye being examined, a field stop disposed at a fundus-conjugate position in the first optical system, a second optical system for reforming the eye fundus image formed near the field stop, and image pickup means that has a plurality of pixels in a matrix array disposed at the position where the image of the eye fundus is formed by the second optical system. The ophthalmic photography apparatus comprises a lens movable within the first optical system along the optical axis for compensation for shifts in the image-formation position due to differences in diopter of the eye being examined; a stop with two apertures disposed within the second optical system or in the vicinity thereof at a position substantially conjugate to the anterior ocular segment of the eye being examined; and a deflecting optical element provided near the imaging surface of the image pickup means; wherein the exit pupil position of the second optical system is set to be at infinity, and the image pickup means and the deflecting optical element are disposed such that the light that is incident upon one pixel column of the image pickup means via the deflecting optical element is only that light that passed through one of the two apertures of the stop, and light from both apertures is incident upon alternate pixel columns of the image pickup means.

The invention further provides an ophthalmic photography apparatus that uses an electronic image pickup means disposed at a position conjugate to the fundus of an eye being examined, comprising an objective lens that forms an image of light reflected from the fundus of an eye being examined; a first image-forming lens disposed behind said objective lens; a photographic stop disposed on the image-side focal surface of the first image-forming lens; a second image-forming lens disposed such that its object-side focal surface coincides with the position of the photographic stop; an optical element disposed on the image-side focal surface of the second image-forming lens for guiding the eye fundus image to the electronic image pickup means; and drive means for moving the first image-forming lens, photographic stop, second image-forming lens, optical element and electronic image pickup means as a unit along the optical axis; wherein the object-side focal surface of the objective lens is brought into coincidence with the anterior ocular segment of the eye being examined, and the first image-forming lens, photographic stop, second image-forming lens, optical element and electronic image pickup means are moved as a unit along the optical axis for focus adjustment.

The present invention has advantages in that the exit pupil position of the optical system that forms an image of the eye fundus on the image pickup means for use in stereoscopic photography is set to infinity, so the angle of incidence of rays to the deflecting optical element becomes constant, and the image for the left eye and the image for the right eye used for stereoscopic viewing are separated and caused to be incident upon the imaging device in alternating pixel columns, and thus the image for the left eye and the image for the right eye are not incident in superposition upon a single pixel column and thus a high-quality image for stereoscopic viewing can be obtained.

In addition, with the present invention, even when the focus is adjusted to compensate for differences in diopter of the eye being examined, the photographic stop disposed at a position conjugate to the anterior ocular segment is always positioned upon the object-side focal surface and the optical system is kept telecentric, so the phenomenon of a stereoscopic view that becomes more concave or convex the nearer to the periphery of the screen is eliminated. In addition, the optical element that guides the left and right images of the eye fundus for stereoscopic viewing to the stipulated pixel column is disposed in front of the image pickup means, and thus a good image of the fundus for stereoscopic viewing can be obtained without any crosstalk of the left and right eye fundus images upon the image pickup surface.

Further features of the invention, its nature and various advantages will be more apparent from the accompanying drawings and following detailed description of the invention.

DESCRIPTION OF THE PREFERRED EMBODIMENTS

The present invention is adapted for use in an ophthalmic photography apparatus able to take photographs for use in stereoscopic viewing. With reference to the following drawings, embodiments of the ophthalmic photography apparatus according to the present invention will now be described in detail based on a fundus camera.

Figure 1:
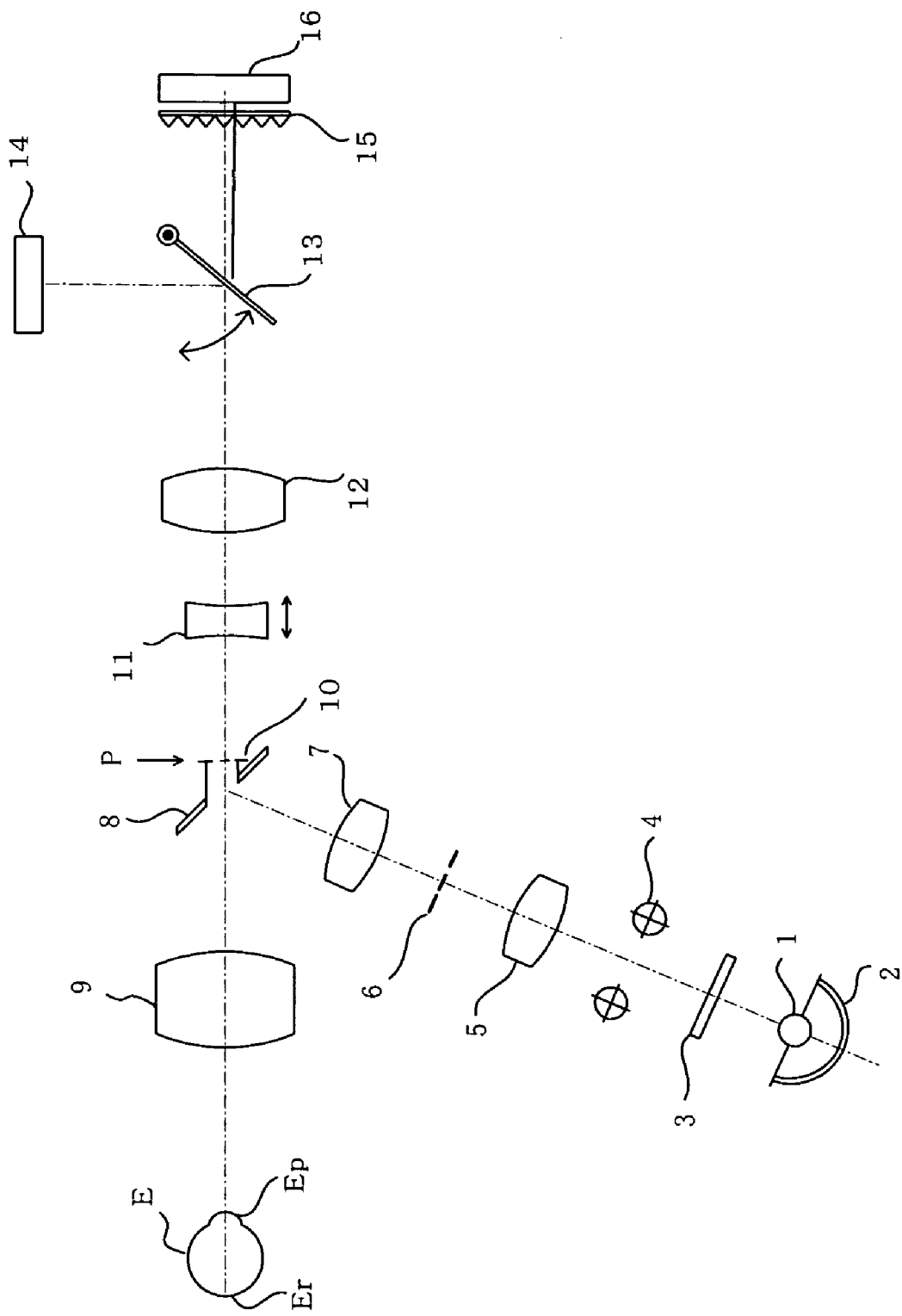
FIG. 1 is an optical view illustrating the optical system according to a first embodiment of the ophthalmic photography apparatus.

FIG. 1 illustrates a first embodiment of the present invention. The illustrated fundus camera comprises an illumination optical system that illuminates the fundus Er of an eye being examined E and a photographic optical system that photographs the eye fundus thus illuminated. In the illumination optical system, light emitted from a halogen lamp or other light source 1 and light reflected from a concave mirror 2 are passed through a visible-light-blocking and infrared-light passing filter 3 and the resulting infrared light is passed through a strobe 4 and a condenser lens 5 to illuminate a ring slit 6 disposed at a position conjugate to the anterior ocular segment (pupil) Ep of the eye being examined E. The illumination light from this slit 6 passes through a lens 7, is reflected by a perforated total-reflection mirror 8 with an aperture in its center, passes through an objective lens 9 and is incident upon the fundus Er through the anterior ocular segment Ep of the eye being examined E, so that the fundus Er is illuminated with infrared light.

Light reflected from the eye fundus Er passes through the objective lens 9 and the aperture of the perforated total-reflection mirror 8 and is incident upon a two-aperture stop 10 with two apertures that is disposed at a position P substantially conjugate to the anterior ocular segment (pupil) of the eye being examined, where it is separated into a light beam for the right optical path and a light beam for the left optical path, which are incident upon a focusing lens 11. This focusing lens 11 is movable along the optical axis, thus compensating for shifts in the position of fundus image formation due to differences among individuals in the diopter of the eye being examined.

The light beams from the fundus then pass through an image-forming lens 12 that forms an image of the fundus of the eye being examined, are reflected by a return mirror 13 and are incident upon an infrared-sensitive observation CCD 14 that is disposed at the position where the image of the eye fundus is formed by the image-forming lens 12, or namely at a position conjugate to the eye fundus Er. When the return mirror 13 is moved away from the optical path, the light beams from the eye fundus are incident upon a visible light-sensitive imaging CCD 16 serving as the photographic means disposed at a position conjugate to the eye fundus Er. The imaging CCD 16 has a large number of pixels disposed in a matrix array, and a lenticular prism 15 serving as the deflecting optical element is disposed near the image pickup surface of the CCD 16.

Figure 2:
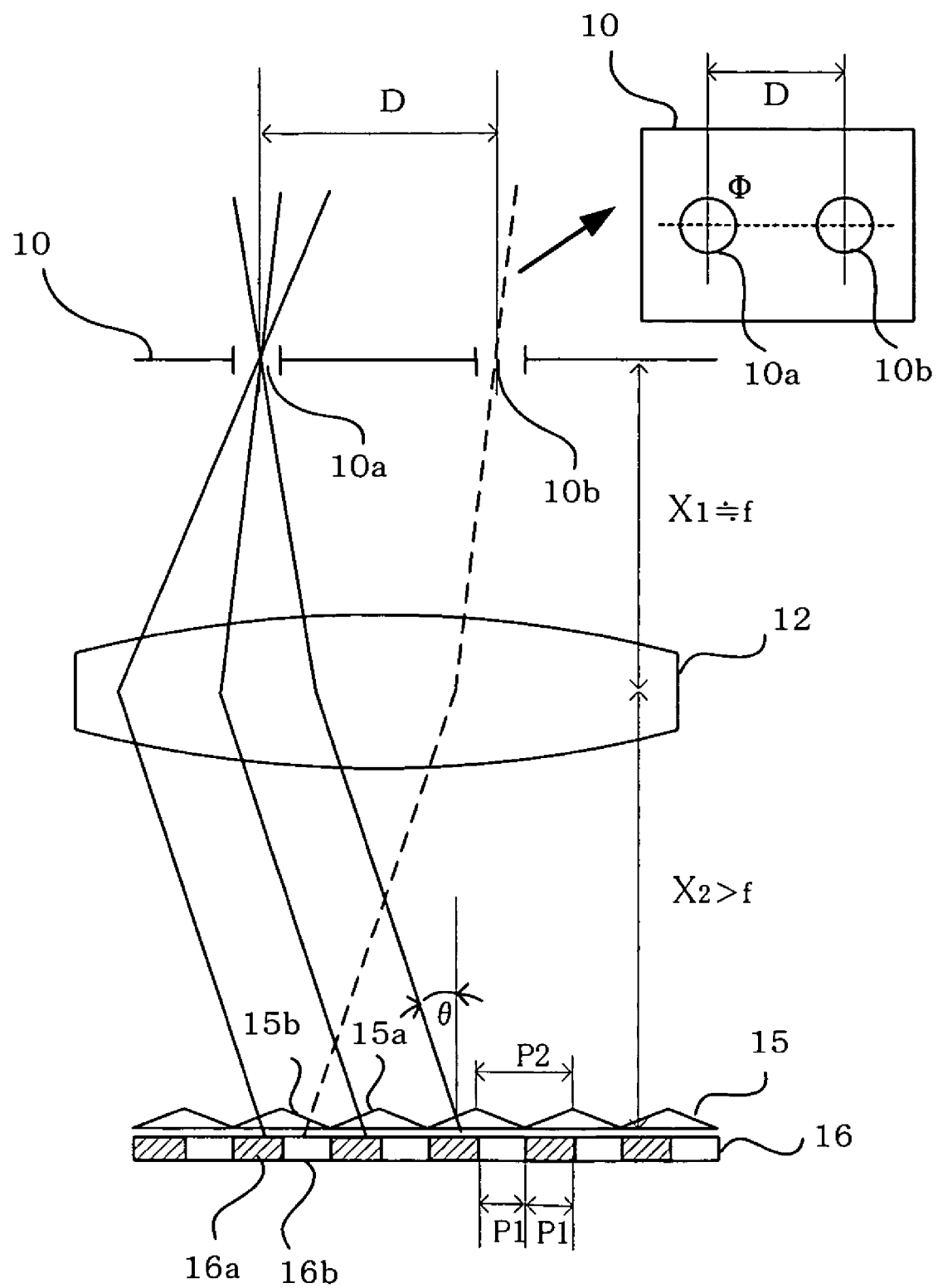
FIG. 2 is an illustrative view showing a state in which light beams passing through the apertures of the two-aperture stop are incident upon a CCD used for photography.

Note that in FIG. 1, the two-aperture stop 10 is illustrated as dividing the light beam vertically in the plane of the paper, and the lenticular prism 15 and imaging CCD 16 are illustrated such that their perpendicular ordering is vertically in the plane of the paper in FIG. 1, but in fact, as shown in FIG. 2, the two-aperture stop 10 divides the light beam in the left-right direction (the direction perpendicular to the plane of the paper in FIG. 1), and the two prism surfaces 15a and 15b of the lenticular prism 15 extend in the direction perpendicular to the plane of the paper in FIG. 2.

Figure 3:
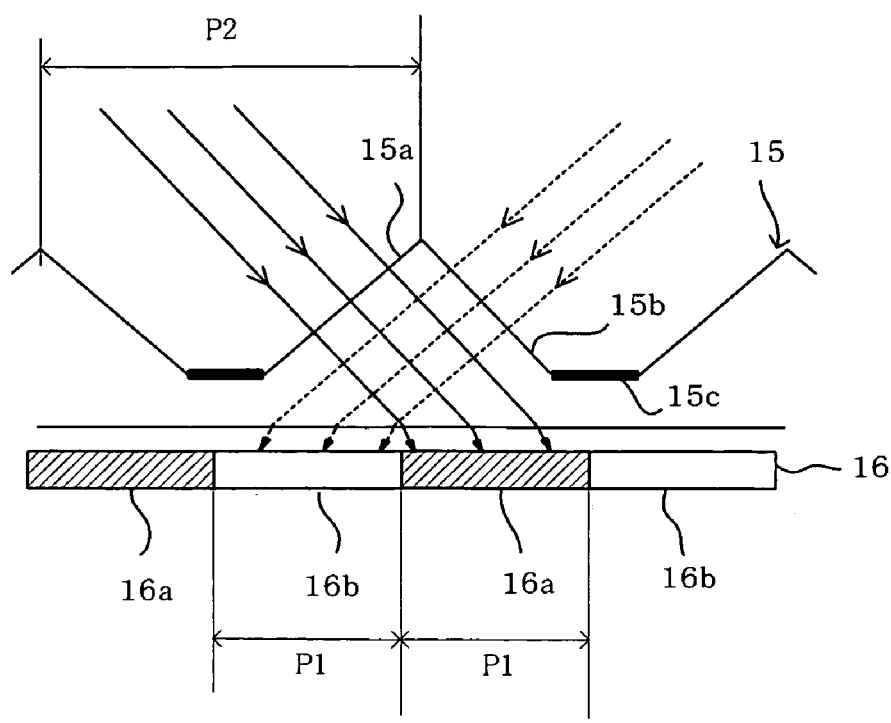
FIG. 3 is an enlargement of the portion of FIG. 2 containing the lenticular prism and the CCD used for photography.

In addition, the position of the exit pupil of the image-forming optical system (focusing lens 11, image-forming lens 12) is set to infinity or thereabouts, and thus as shown in FIGS. 2 and 3 (In FIG. 2, focusing lens 11 is omitted for simplicity. Or, lens 12 may be considered to be an optical system that combines the focusing lens and the image-forming lens.), the light beams passing through one aperture 10a of the two-aperture stop at a substantially pupil-conjugate position become substantially parallel light beams after passing through image-forming lens 12, and upon being incident upon one of the prism surfaces 15a of the lenticular prism 15, are incident upon the odd-numbered pixel columns (the shaded portions) 16a of the imaging CCD 16. Similarly, the light beams passing through the other aperture 10b of the two-aperture stop become substantially parallel light beams after passing through image-forming lens 12, and upon being incident upon the other of the prism surfaces 15b of the lenticular prism 15, are incident upon the even-numbered pixel columns 16b of the imaging CCD 16. Note that the thick solid-line portion 15c in FIG. 3 illustrates a shading area.

Such light-incidence characteristics may be obtained, for example, if the distance between the two apertures 10a and 10b of the two-aperture stop 10, or namely the pupil separation distance D is set to D=3 mm, the diameter $\Phi$ of apertures 10a and 10b is $\Phi$=0.5 mm, the focal length f of image-forming lens 12 is f=20 mm, the imaging CCD 16 is made a 3-inch CCD, the distance X1 between the two-aperture stop 10 and the image-forming lens 12 is approximately equal to f, or namely the two-aperture stop 10 is positioned at or near the focal length of image-forming lens 12, and the distance X2 between the image-forming lens 12 and the lenticular prism 15 and imaging CCD 16 is set to a value greater than f. At this time, the angle of incidence $\theta$ of the light beam from the image-forming lens 12 upon the lenticular prism 15 becomes $\theta$=4.3°, and the prism angles are set such that each of the parallel light beams is incident substantially perpendicular to the prism surfaces 15a and 15b of the lenticular prism 15. In addition, the pixel pitch (pixel width) P1 in the row direction of the imaging CCD 16 (the left-right direction in FIGS. 2 and 3) is set to approximately half the prism pitch (distance between the vertices of prisms) P2 of the lenticular prism 15.

In such a configuration, the light source 1 is turned on to illuminate the fundus Er of the eye being examined E with infrared light, the light reflected from the fundus is guided to the observation CCD 14 and this image is observed to perform alignment, while at the same time the focusing lens 11 is moved along the optical axis to adjust the focus.

Once alignment and focusing are complete, the strobe 4 emits light and the return mirror 13 is moved out of the optical path. The light beam from the eye fundus illuminated with strobe light passes through the objective lens 9 and the aperture of the perforated total-reflection mirror 8, is incident upon the two-aperture stop 10 and separated into a light beam for the right optical path and a light beam for the left optical path, which are incident upon the focusing lens 11, and thus an image of the eye fundus is formed by the image-forming lens 12 on the image pickup surface of the CCD 16 via the lenticular prism 15.

The position of the exit pupil of the image-forming optical system made up of the focusing lens 11 and the image-forming lens 12 is set to infinity or thereabouts, and thus as shown in FIGS. 2 and 3, the light beams passing through aperture 10a of the two-aperture stop become substantially parallel light beams after passing through image-forming lens 12, and upon being incident upon one of the prism surfaces 15a of the lenticular prism 15, are incident upon the odd-numbered pixel columns 16a of the imaging CCD 16. Similarly, the light beams passing through aperture 10b of the two-aperture stop become substantially parallel light beams after passing through image-forming lens 12, and upon being incident upon the other of the prism surfaces 15b of the lenticular prism 15, are incident upon the even-numbered pixel columns 16b of the imaging CCD 16. In addition, the pixel pitch (pixel width) P1 in the row direction of the imaging CCD 16 (the left-right direction in FIG. 4) is set to approximately half the prism pitch (distance between the vertices of prisms) P2 of the lenticular prism 15, so the pixel columns Rj (j=1 to n) of the imaging CCD 16 receive only light passing through aperture 10a of the two-aperture stop 10 and none of the light passing through the other aperture 10b. Similarly, the pixel columns Lj (j=1 to n) receive only light passing through aperture 10b of the two-aperture stop 10 and none of the light passing through the other aperture 10a. Thus, light from the two apertures 10a and 10b is incident alternately upon the pixel columns Rj and Lj.

Figure 4:
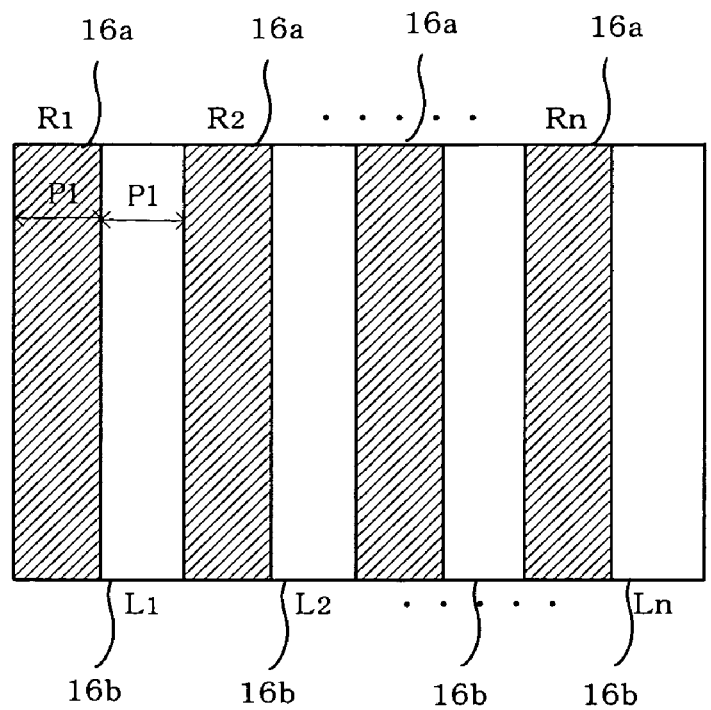
FIG. 4 is an illustrative view showing the incidence of rays into the various pixel columns of the CCD used for photography.

The image distribution on the image pickup surface of the Imaging CCD 16 as such is illustrated in FIG. 4, where R1, R2 . . . Rn are the odd-numbered pixel columns 16*a* and L1, L2 . . . Ln are the even-numbered pixel columns 16*b*, and each of the pixels has the width P1 in the row direction.

Figure 5:
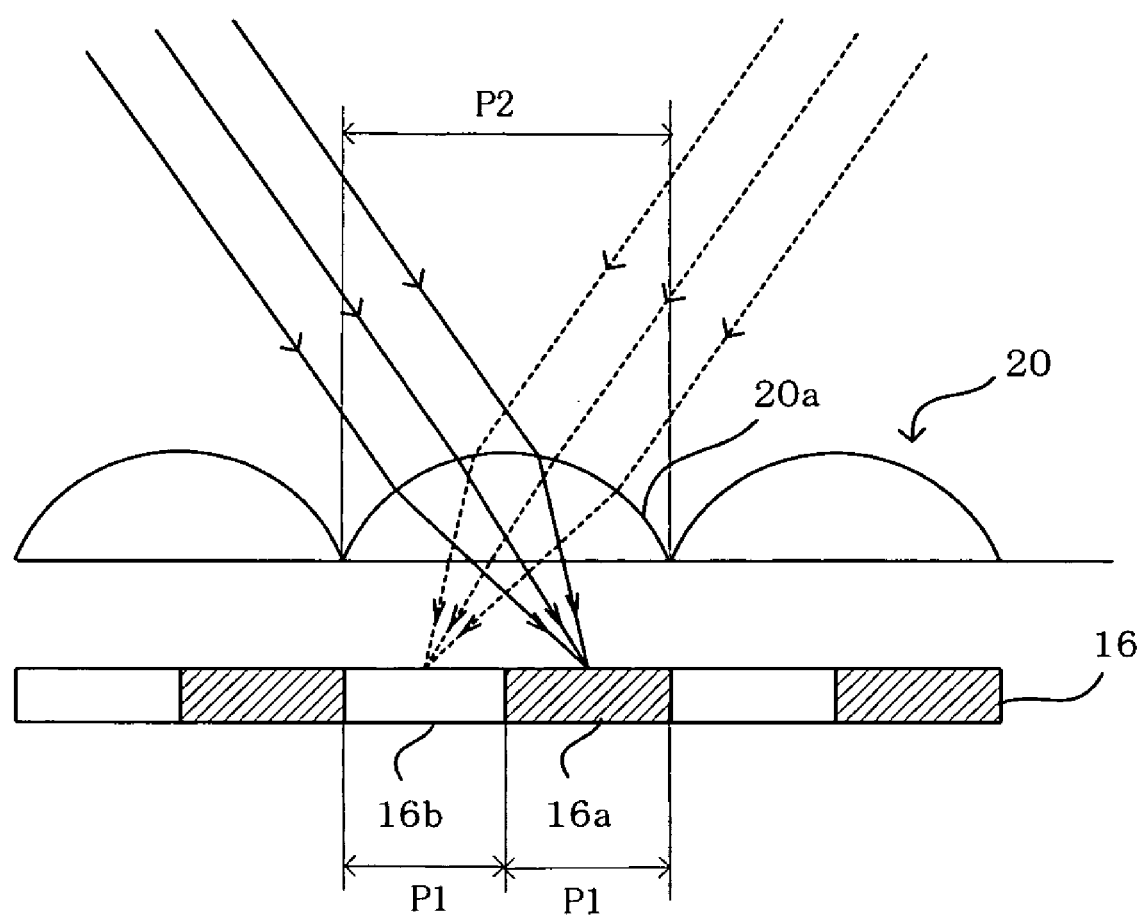
FIG. 5 is an enlargement corresponding to FIG. 3 but when a lenticular lens is used.

Alternatively, a lenticular lens 20 as illustrated on FIG. 5 can be used instead of the lenticular prism 15. This lenticular lens 20 comprises an array of semicylindrical lenses 20*a* extending perpendicular to the plane of the paper in FIG. 5 equally spaced in the left-right direction at a pitch P2 (two times the pixel pitch P1), so the light beams passing through aperture 10*a* of the two-aperture stop 10 become substantially parallel light beams after passing through image-forming lens 12, are refracted by the semicylindrical lenses 20*a* of the lenticular lens 20 and converge upon pixel columns 16*a* of the CCD 16. Similarly, the light beams passing through aperture 10*b* of the two-aperture stop 10 become substantially parallel light beams after passing through image-forming lens 12, are refracted by the same semicylindrical lenses 20*a* and converge upon the pixel columns 16*b* to the left of pixel columns 16*a* of the CCD 16, and thus the same sort of effect as with a lenticular prism 15 can be obtained.

Note that the images picked up by the Imaging CCD 16 may be displayed in stereo by a commercial lenticular-type monitor, parallax barrier-type monitor or other such display means, or it can be viewed stereoscopically using polarized glasses.

In addition, the specifications of the various optical elements described above assume a pupil image formation magnification of approximately 1×, and under these conditions, the photographed scope has a field angle of approximately 10°, so any cupping of the optic disc can be viewed stereoscopically, making this an effective means in the diagnosis of glaucoma.

Figure 6:
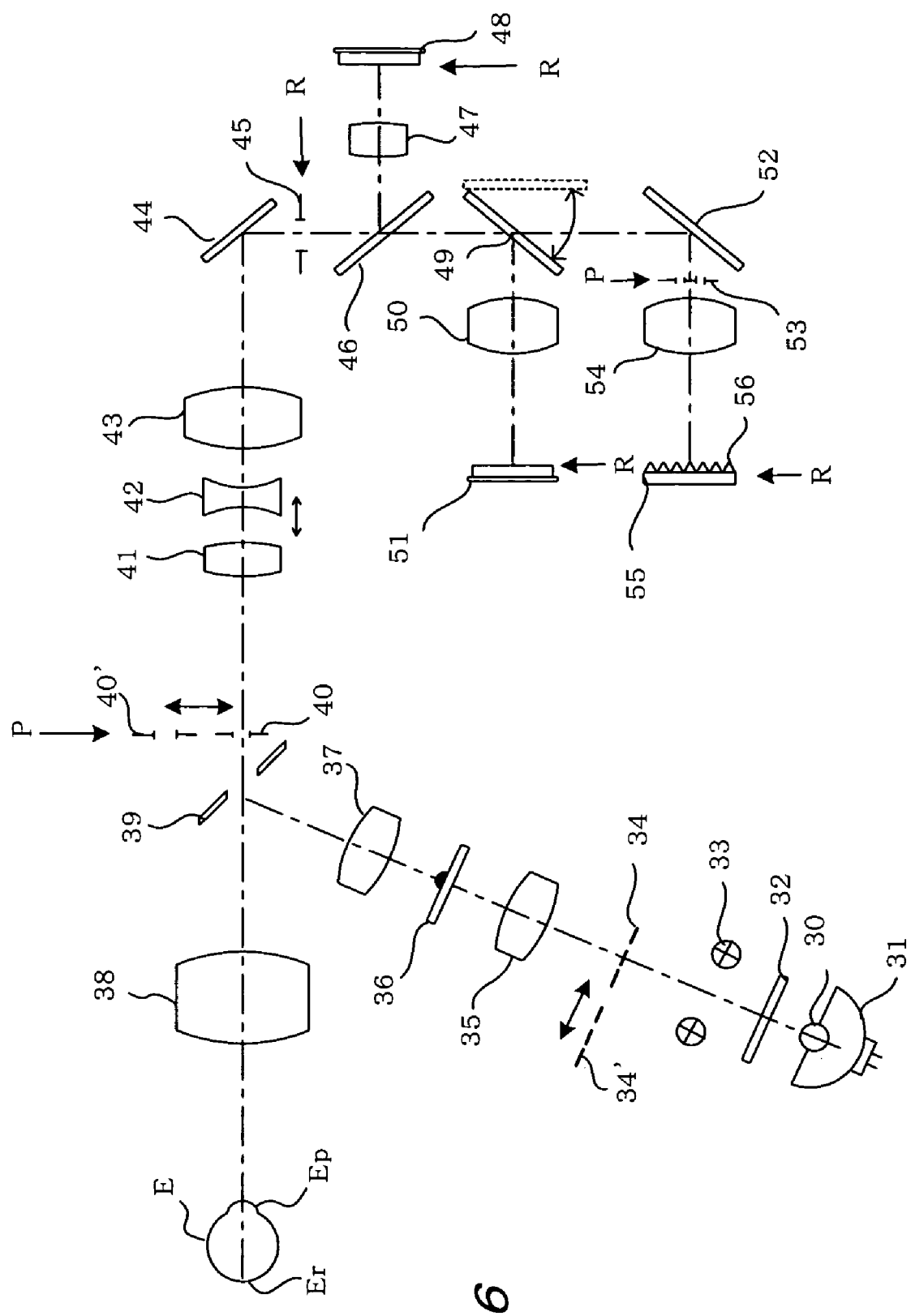
FIG. 6 is an optical view showing the optical system according to a second embodiment of the ophthalmic photography apparatus.

FIG. 6 shows another embodiment enabling both monocular and stereoscopic photography.

In FIG. 6, light emitted from a halogen lamp or other light source 30 and light reflected from a concave mirror 31 is passed through a visible-light-blocking and infrared-light-passing filter 32 and the resulting infrared light is passed through a strobe 33 to illuminate a ring slit 34 disposed at a position conjugate to the anterior ocular segment (pupil) Ep of the eye being examined E. During stereoscopic photography, this ring slit 34 is replaced with a stereoscopic illumination stop 34'. The illumination light from the ring slit 34 or stereoscopic illumination stop 34' passes through a lens 35, black-spot plate 36 and relay lens 37, is reflected by a perforated total-reflection mirror 39 with an aperture in its center, passes through an objective lens 38 and is incident upon the fundus Er through the anterior ocular segment Ep of the eye being examined E, so that the eye fundus Er is illuminated with infrared light.

Light reflected from the eye fundus Er is received via objective lens 38, passes through the aperture of the perforated total-reflection mirror 39 and is incident upon a photographic stop 40 that is disposed at a position P conjugate to the anterior ocular segment (pupil) Ep and passes through a lens 41 and focusing lens 42. This focusing lens 42 is movable along the optical axis, thus compensating for shifts in the position of fundus image formation due to differences among individuals in the diopter of the eye being examined. Note that the photographic stop 40 is replaced with a photographic stop 40' having a greater aperture during stereoscopic photography.

The light beams from the eye fundus then pass through a lens 43, are reflected by a mirror 44, are incident upon an infrared-light-reflecting and visible-light-passing mirror 46 via a field stop 45 disposed at a position R conjugate to the eye fundus Er, and the infrared light reflected by the infrared-light-reflecting and visible-light-passing mirror 46 passes through an image-forming lens 47 and is incident upon an infrared-sensitive CCD for observation 48 serving as the photographic means. On the other hand, the visible light that passes through the mirror 46 is reflected by a return mirror 49, passes through an image-forming lens 50 and is incident upon a visible light-sensitive CCD for monocular photography 51 serving as the imaging device.

When stereoscopic photography is to be performed, the return mirror 49 is moved away from the optical path, visible light passing through the mirror 46 is reflected by a mirror 52, passes through a two-aperture stop 53 that is disposed at a position P substantially conjugate to the anterior ocular segment (pupil) and through an image-forming lens 54, and is incident upon a visible light-sensitive CCD for stereoscopic photography 55 that serves as the image pickup means. A lenticular prism 56 serving as the deflecting optical element is disposed near the image pickup surface of the CCD for stereoscopic photography 55. The two-aperture stop 53, lenticular prism 56 and CCD for stereoscopic photography 55 correspond respectively to the two-aperture stop 10, lenticular prism 15 and imaging CCD 16 of the first embodiment.

In this image-forming optical system, the position conjugate to the fundus Er of the eye being examined E is illustrated as R and the position conjugate to the anterior ocular segment (and pupil in particular) Ep is indicated as P, and the objective lens 38, lenses 41, 43 and the like constitute a first optical system that forms an image of the fundus of the eye being examined upon the field stop 45, while the image-forming lenses 50 and 54 constitute a second optical system that reforms the eye fundus image formed near the field stop 45 by the first optical system upon the CCD for monocular photography 51 and the CCD for stereoscopic photography 55. In addition, taking the CCD for stereoscopic photography 55 to be a first photographic means, the return mirror 49 is an optical path dividing means disposed between the field stop 45 and the first photographic means, and thus depending on its position, the light beams from the eye being examined are switched and selectively guided to the first photographic means (CCD for stereoscopic photography 55) or the second photographic means (CCD for monocular photography 51).

With such a configuration, an infrared image of the eye fundus is formed upon the CCD for observation 48, so the alignment and focusing operations are performed while observing the image from the CCD for observation 48 with a monitor (not shown).

Once alignment and focusing are complete, the strobe 33 emits light and, during monocular photography, the ring slit 34, photographic stop 40 and return mirror 49 form the optical path, so the light beams from the eye fundus are incident upon the CCD for monocular photography 51 and the eye fundus is photographed by the CCD for monocular photography 51.

On the other hand, during stereoscopic photography, the return mirror 49 is moved out of the optical path and at this time, the illumination stop is switched to the stereoscopic illumination stop 34' and the photographic stop is switched to the stereoscopic photographic stop 40'. The light beam from the eye fundus is separated by the two-aperture stop 53 into a light beam for the right optical path and a light beam for the left optical path, and images of these light beams are formed upon the CCD for stereoscopic photography 55 via the lenticular prism 56, and thus images of the eye fundus for stereoscopic viewing are photographed.

The position of the exit pupil of the second optical system made up of the image-forming lens 54 is set to infinity or thereabouts, in the same manner as the optical system of image-forming lens 12 according to the first embodiment. The light beams passing through one aperture of the two-aperture stop 53 thus become substantially parallel light beams after passing through image-forming lens 54, and upon being incident upon one of the prism surfaces of the lenticular prism 56, are incident upon the odd-numbered pixel columns of the CCD for stereoscopic photography 55. Similarly, the light beams passing through the other aperture of the two-aperture stop 53 become substantially parallel light beams after passing through image-forming lens 54, and upon being incident upon the other of the prism surfaces of the lenticular prism 56, are incident upon the even-numbered pixel columns of the CCD for stereoscopic photography 55. This relationship is equivalent to that of FIG. 3, where the lenticular prism 15 is replaced with lenticular prism 56 and the imaging CCD 16 is replaced with CCD for stereoscopic photography 55, and in the same manner as in the first embodiment, the pixel pitch (pixel width) P1 in the row direction of the CCD for stereoscopic photography 55 is set to approximately half the prism pitch (distance between the vertices of prisms) P2 of the lenticular prism 56, so one half of the pixel columns of the CCD for stereoscopic photography 55 receive only light passing through one of the apertures of the two-aperture stop 53 and none of the light passing through the other aperture. Thus, light from the two apertures of the two-aperture stop 53 are incident alternately upon the pixel columns. This relationship is also the same as that in the first embodiment so the same meritorious effects as in the first embodiment are obtained.

In addition, in the same manner as in the first embodiment, a lenticular lens 20 as illustrated on FIG. 5 can be used instead of the lenticular prism 56.

In addition, the images picked up by the CCD for stereoscopic photography 55 may be displayed in stereo by a commercial lenticular-type monitor, parallax barrier-type monitor or other such display means, or it can be viewed stereoscopically using polarized glasses.

In the embodiments described above, there are cases wherein, when the focusing lens 11 or focusing lens 42 is manipulated to adjust the focus depending on the diopter of the eye being examined, the optical system cannot be kept telecentric, so that crosstalk occurs in the eye fundus images upon the image pickup surface and thus good images for stereoscopic viewing cannot be obtained. An embodiment that solves this problem will now be described based on FIG. 7.

Figure 7:
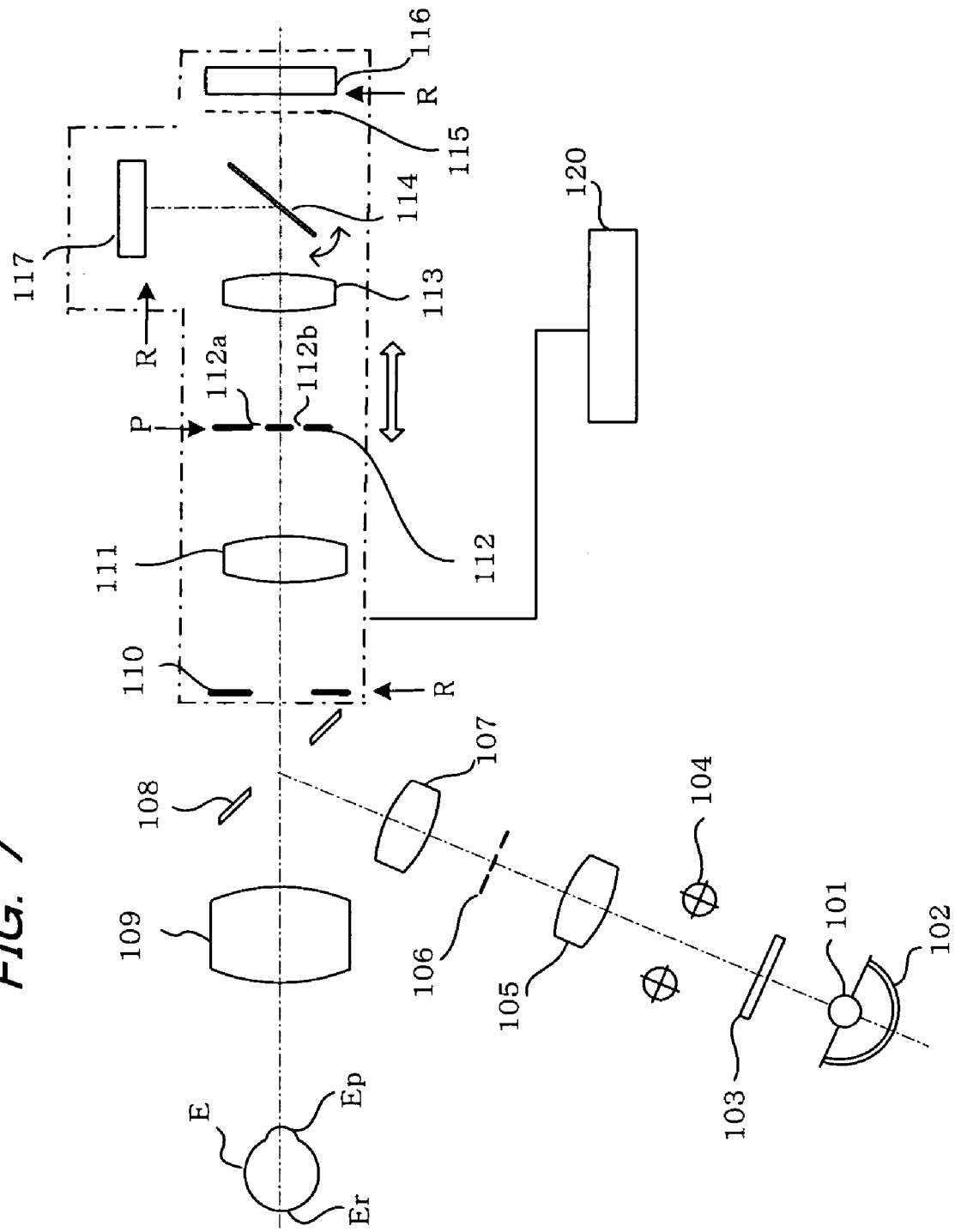
FIG. 7 is an optical view showing the optical system of an ophthalmic photography apparatus according to the present invention.

Like the embodiment illustrated in FIG. 1, the fundus camera shown in FIG. 7 comprises an illumination optical system that illuminates the fundus Er of an eye being examined E. In this illumination optical system, light emitted from a halogen lamp or other light source 101 and light reflected from a concave mirror 102 is passed through a visible-light-blocking and infrared-light-passing filter 103 and the resulting infrared light is passed through a strobe 104 and a condenser lens 105 to illuminate a stereoscopic viewing slit 106 disposed at a position conjugate to the anterior ocular segment (pupil) Ep of the eye being examined E. The illumination light from this slit 106 passes through a lens 107, is reflected by a perforated total-reflection mirror 108 with an aperture in its center, passes through an objective lens 109 and is incident upon the fundus Er through the anterior ocular segment Ep of the eye being examined E, so that the fundus Er is illuminated with infrared light.

Light reflected from the eye fundus Er passes through the objective lens 109 and the aperture of the perforated total-reflection mirror 108, goes through a photographic mask 110 that determines the range of the eye fundus to be photographed and is incident upon a first image-forming lens 111. The photographic mask 110 is disposed at a position R conjugate to the eye fundus between the objective lens 109 and the first image-forming lens 111. A photographic stop (two-aperture stop) 112 with two circular apertures 112a and 112b is disposed on the image-side focal surface of the first image-forming lens 111. The eye fundus image passing through the photographic stop 112 is divided by the apertures 112a and 112b of the photographic stop 112 into a light beam for the right optical path and a light beam for the left optical path and is then incident upon a second image-forming lens 113. The photographic stop 112 is disposed upon the object-side focal surface of the second image-forming lens 113, and the light beams that pass through the second image-forming lens 113 are reflected by a return mirror 114 and are incident upon an infrared-sensitive CCD for observation 117 that is disposed at a position conjugate to the eye fundus Er and the photographic mask 110.

When the return mirror 114 is moved away from the optical path, the light beams from the eye fundus are incident upon a visible light-sensitive CCD for photography 116 serving as an electronic image pickup means disposed at a position conjugate to the eye fundus Er and the photographic mask 110. The CCD for photography 116 has a large number of pixels disposed in a matrix array, and a lattice barrier 115 as an optical element is disposed near the image pickup surface of the CCD for photography 116. This lattice barrier 115 is a lattice-type light-shading plate with a plurality of parallel slit-shaped apertures disposed at equal intervals, and is disposed on the image-side focal surface of the second image-forming lens 113, while the photographic stop 112 is disposed on the object-side focal surface of this second image-forming lens 113 as described above, thus constituting a telecentric optical system.

Note that in FIG. 7, the photographic stop 112 is illustrated as dividing the light beam vertically in the plane of the paper, and the direction in which the slits of the lattice barrier 115 extend is illustrated as being in a direction perpendicular to the paper, but in fact, the photographic stop 112 divides the light beam in the left-right direction (the direction perpendicular to the plane of the paper in FIG. 7), and the slits of the lattice barrier 115 extend in a direction parallel to the plane of the paper.

FIGS. 8a, 8b, 9a and 9b illustrate the paths of the rays of the pupil image and eye fundus image, but in order to avoid complexity, the illumination optical system, return mirror and observation optical system of the CCD for observation 117 illustrated in FIG. 7 are omitted.

Figure 8A:
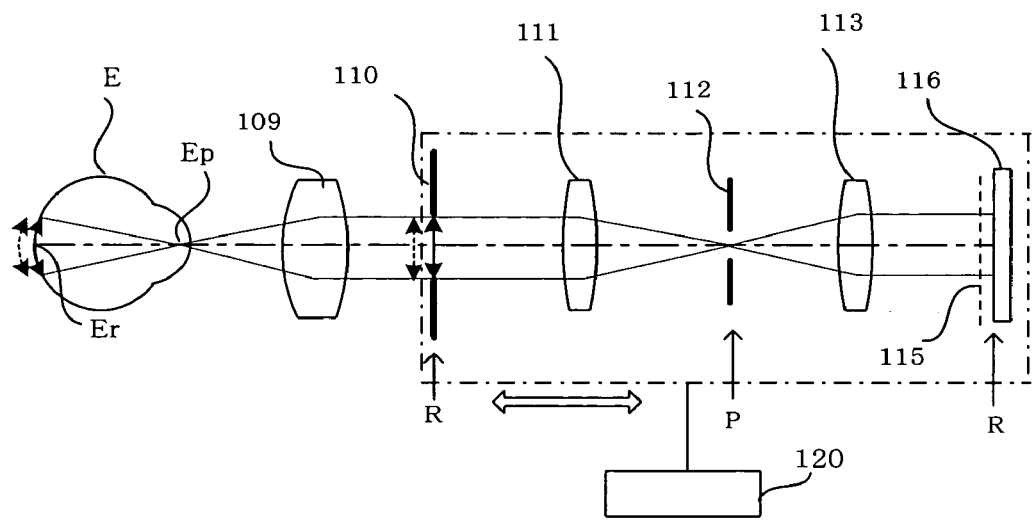
FIG. 8a is an illustrative view showing the path of rays of the pupil image.
Figure 9A:
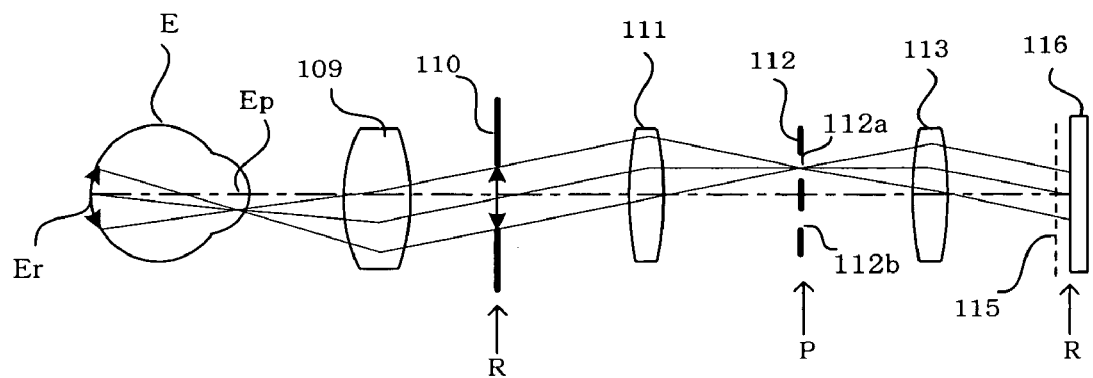
FIG. 9a is an illustrative view showing the path of the principal ray based on the pupil image.

When alignment is complete, the object-side focal surface of the objective lens 109 lies upon the anterior ocular segment Ep or the vicinity thereof, and the ray paths of the pupil image at that time are shown in FIG. 8a and FIG. 9a. The anterior ocular segment lies upon the object-side focal surface of the objective lens 109 so the light beam making up the pupil image passing through the objective lens 109 becomes a telecentric light beam, and the pupil image is formed by the first image-forming lens 111 at the position of the photographic stop 112 disposed at its image-side focal surface. Accordingly, the photographic stop 112 is at a position conjugate to the pupil and the photographic stop 112 is disposed upon the object-side focal surface of the second image-forming lens 113, so the light beams passing through the second image-forming lens 113 become telecentric light beams. Note that FIG. 8a shows the ray passing through the optical axis, so for the sake of simplicity, the photographic stop 112 is shown as a one-aperture stop with an aperture in its center.

Figure 8B:
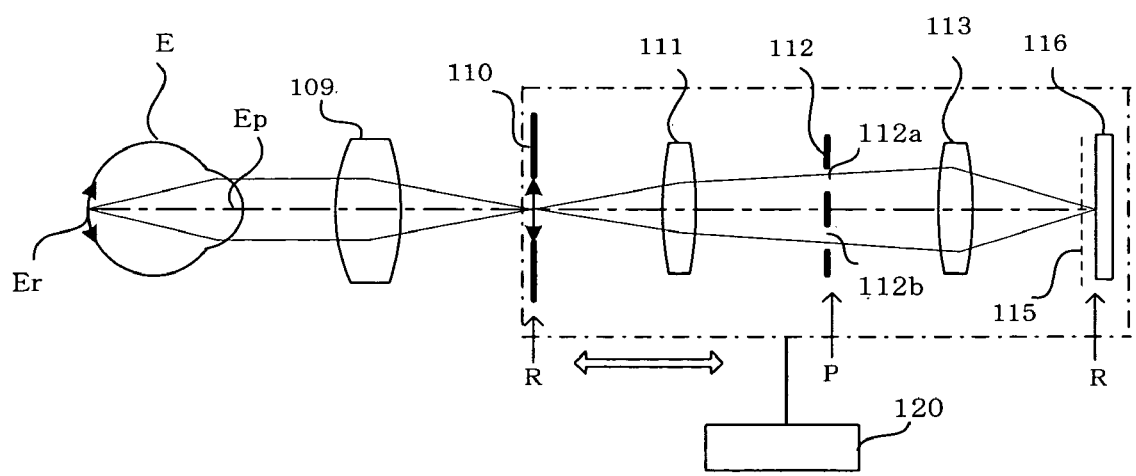
FIG. 8b is an illustrative view showing the path of rays of the fundus image.
Figure 9B:
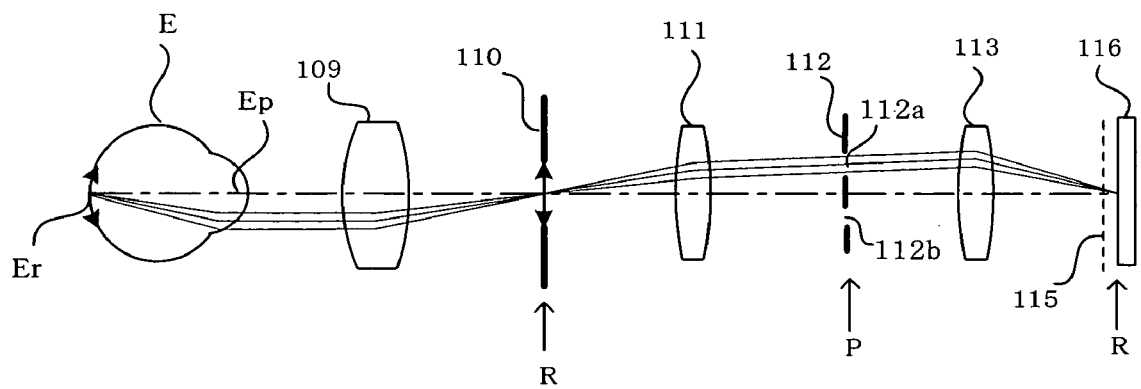
FIG. 9b is an illustrative view showing the path of the principal ray based on the fundus image.

On the other hand, FIGS. 8b and 9b show the ray paths of the eye fundus image. The focus is adjusted so that the photographic mask 110 lies at the position of the eye fundus image formed by the objective lens 109 and so that the eye fundus image is formed upon the CCD for photography 116. The position of the eye fundus image formed by he objective lens 109 will be different depending on the diopter of the eye being examined, and this is adjusted by moving the image-forming lens in the direction of the optical axis so that the eye fundus image is formed upon the CCD for photography 116, but in the present invention, in order to maintain the pupil-conjugate relationship illustrated in FIGS. 8a and 9a and keep the image-side optical system telecentric in the second image-forming lens, the photographic mask 110, first image-forming lens 111, photographic stop 112, second image-forming lens 113, lattice barrier 115, CCD for photography 116, along with the return mirror 114 and CCD for observation 117 that constitute the observation optical system shown in FIG. 7 are formed as a single unit and moved as a unit in the direction of the optical axis as indicated by the double-lined arrow either manually or with a motor drive or other drive means 120. The portion moved by this drive means 120 is shown in FIGS. 7 through 9 enclosed by a one-dot chain line, and the position conjugate to the eye fundus is indicated by R while the position conjugate to the pupil is indicated by P.

Figure 10:
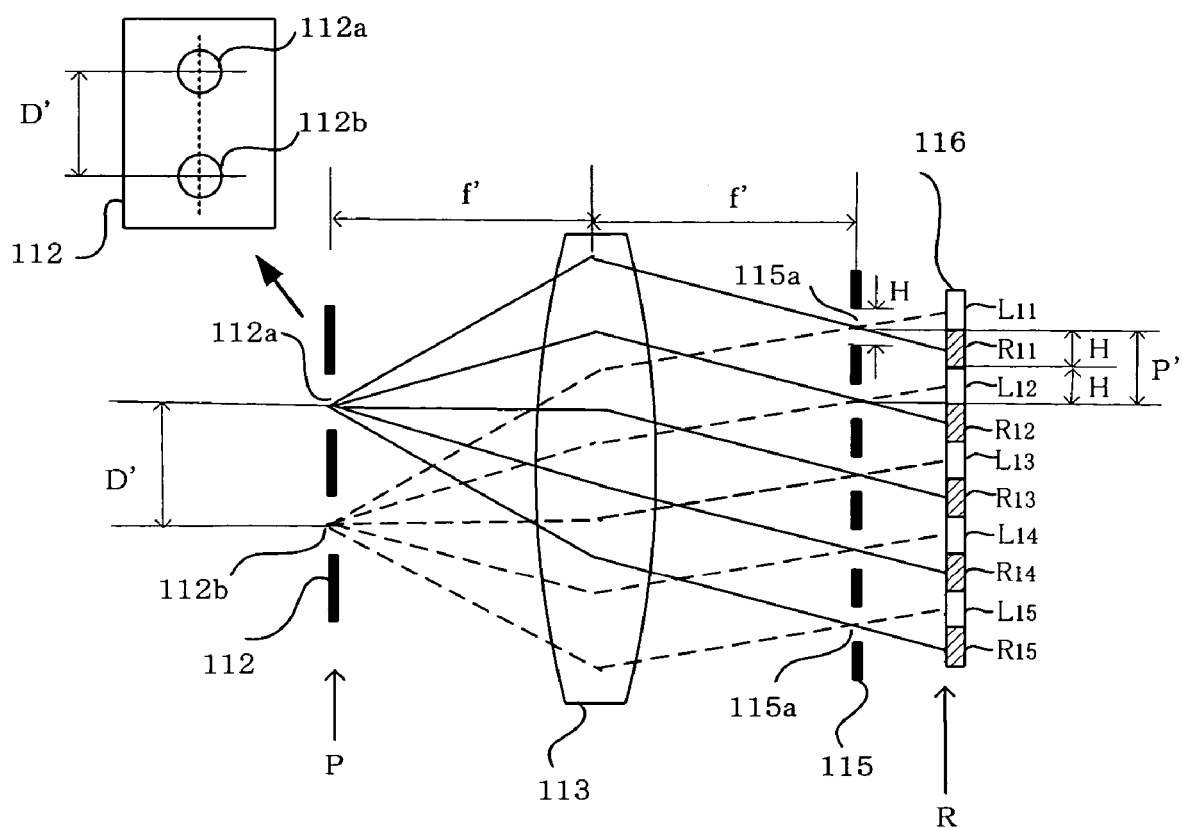
FIG. 10 is an illustrative view showing the paths of the rays passing through the apertures in the photographic stop.
Figure 11A:
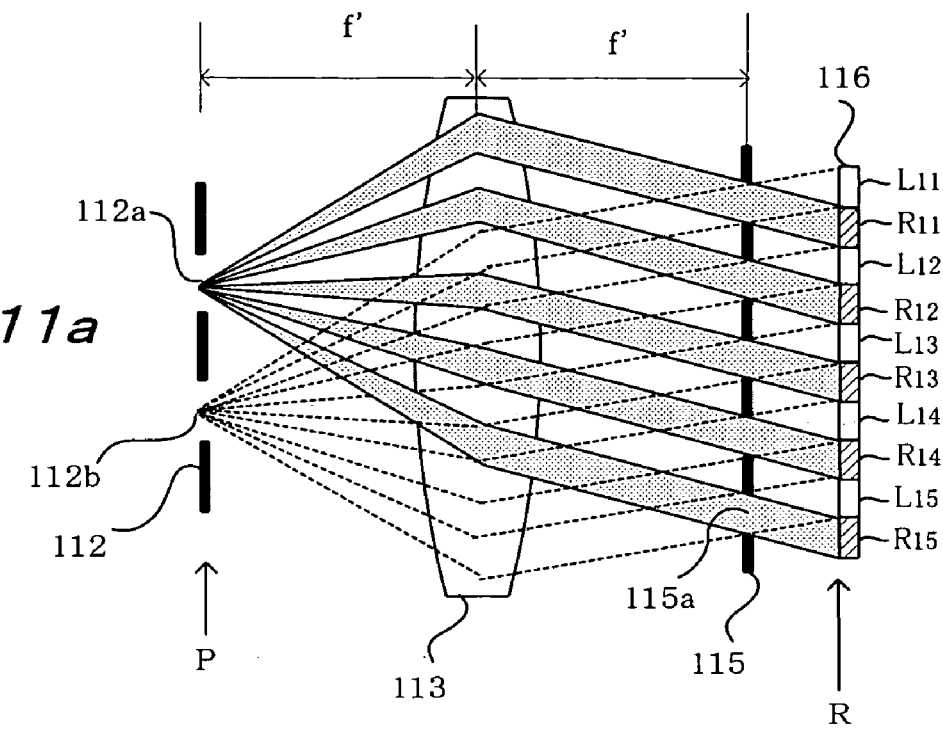
FIG. 11a is an illustrative view showing the paths of the rays of the pupil image passing through the apertures in the photographic stop.
Figure 11B:
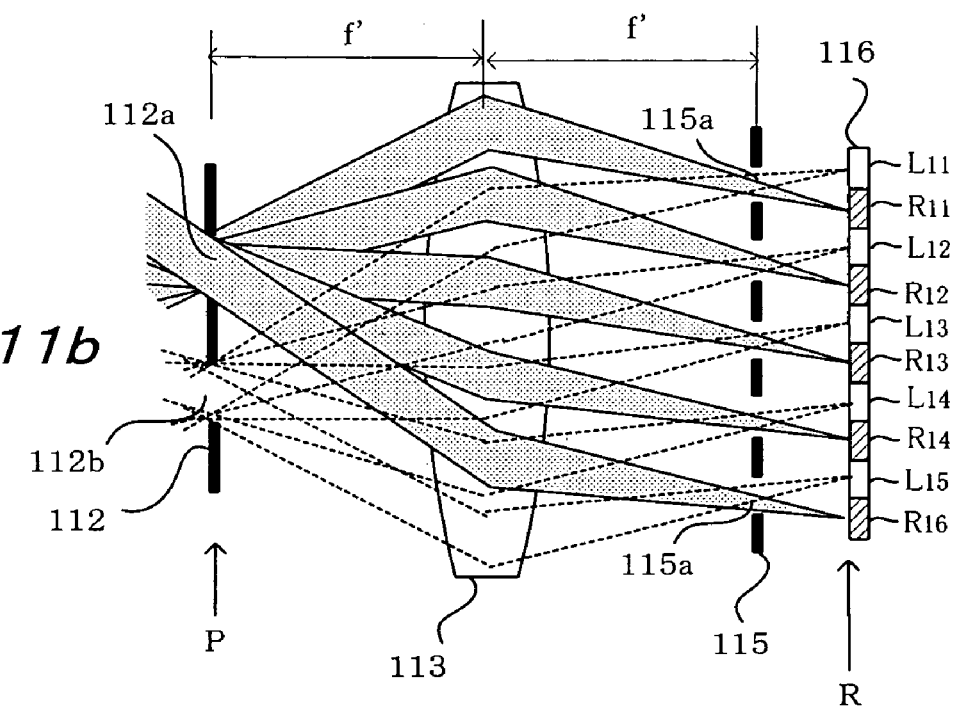
FIG. 11b is an illustrative view showing the paths of the rays of the fundus image passing through the apertures in the photographic stop.

In addition, FIGS. 10, 11a and 11b show the configuration after of the photographic stop 112 in detail. As shown in FIG. 10, the lattice barrier 115 is disposed such that the width H of each of a plurality of slits 115a extending perpendicular to the plane of the paper has the same value as the width H of the pixels of the CCD for photography 116, and the pitch P' of the slits of the lattice barrier 115 is twice the pixel pitch of the CCD for photography 116, so the position of the center of each of the slits 115a of the lattice barrier 115 roughly coincides with the position of the boundary between two adjacent pixels of the CCD for photography 116. In addition, in the figure, D' is the distance between the two apertures 112a and 112b of the photographic stop 112, or namely the pupil separation distance, while f' indicates the focal length of the second image-forming lens 113. As described above, the photographic stop 112 is disposed upon the object-side focal surface of the second image-forming lens 113, while the lattice barrier 115 is disposed upon its image-side focal surface.

In such a configuration, the light source 101 is turned on to illuminate the fundus Er of the eye being examined E with infrared light, the light reflected from the fundus is guided to the CCD for observation 117 and this image is observed to perform alignment, while at the same time the drive means 120 is used to move the portions 110-117 enclosed by one-dot chain lines on FIGS. 7-9 along the optical axis to adjust the focus.

As shown in FIGS. 8a and 9a, alignment is performed so that the object-side focal surface of the objective lens 109 is aligned with the position of the anterior ocular segment (pupil), or comes close thereto. In addition, focusing is performed by using the drive means 120 to move the photographic mask 110, first image-forming lens 111, photographic stop 112, second image-forming lens 113, lattice barrier 115, CCD for photography 116 and also the return mirror 114 and CCD for observation 117 as a unit, so that the photographic mask 110 comes to the position of the eye fundus image formed by the objective lens 109, as shown in FIGS. 8b and 9b. At this time, the photographic mask 110 is in a conjugate relationship with the CCD for observation 117 and CCD for photography 116, so a clear image of the eye fundus is formed on the CCD for observation 117, and thus one can confirm that the system is in focus. In addition, when the return mirror 114 is moved out of the optical path, a clear image of the eye fundus can be photographed with the CCD for photography 116.

Once alignment and focusing are complete in this manner, the return mirror 114 is moved out of the optical path and the strobe 104 emits light. The light beam from the eye fundus illuminated with strobe light passes through the objective lens 109, the aperture of the perforated total-reflection mirror 108, the photographic mask 110 and the first image-forming lens 111 and is incident upon the photographic stop 112, where it is separated by its apertures 112a and 112b into a light beam for the right optical path and a light beam for the left optical path.

Figure 12A:
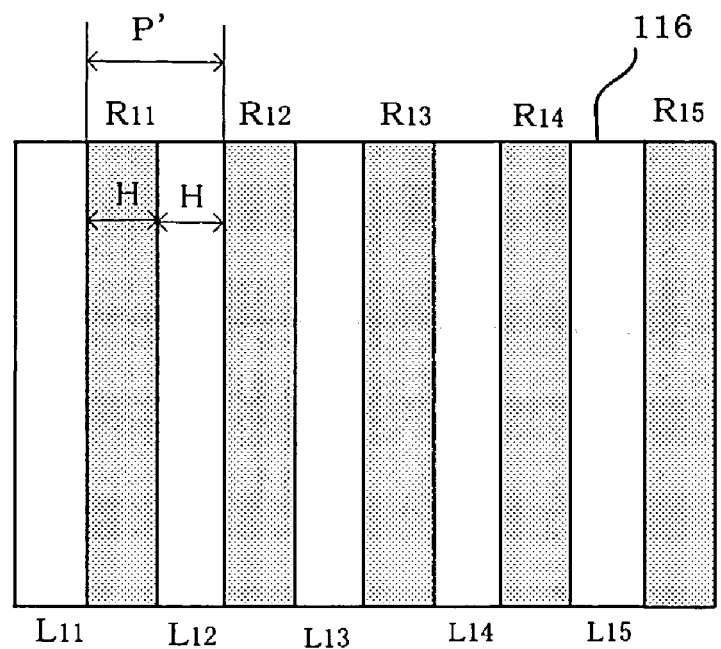
FIG. 12a is an illustrative view showing the layout of the pixel columns of a CCD used for photography.

As shown in FIG. 11a, the light beams (pupil image) for the right eye for stereoscopic viewing passing through aperture 112a indicated by solid lines pass through the second image-forming lens 113 and then become nearly parallel light beams (telecentric light beams), are incident upon the slits 115a of the lattice barrier 115 and then are incident upon the columns of pixels for the right eye for stereoscopic viewing (the portions indicated by shading) R11 through R15 of the CCD for photography 116 shown in FIG. 12a. Similarly, the light beams (pupil image) for the left eye for stereoscopic viewing passing through aperture 112b indicated by dashed lines pass through the second image-forming lens 113 and then become nearly parallel light beams or telecentric light beams, are incident upon the slits 115a of the lattice barrier 115 and then are incident upon the columns of pixels for the left eye for stereoscopic viewing (the portions not shaded) L11 through L15 of the CCD for photography 116.

In addition, as shown in FIG. 11b, the eye fundus image for the right eye for stereoscopic viewing passing through aperture 112a is formed on pixel columns R11 through R15 of the CCD for photography 116, while the eye fundus image for the left eye for stereoscopic viewing passing through aperture 112b is formed on pixel columns L11 through L15. FIG. 12a shows a schematic diagram of the arrangement of these pixel columns R11 through R15 and pixel columns L11 through L15 of the CCD for photography 116.

In this manner, in the present invention, focus adjustment is performed by moving the photographic mask 110, first and second image-forming lenses 111 and 113, photographic stop 112, lattice barrier 115, CCD for photography 116 (and also the return mirror 114 and CCD for observation 117) as a unit, so for example, even if focus adjustment is performed to compensate for differences among individuals in the diopter of the eye being examined, the position P conjugate to the anterior ocular segment (the position of the photographic stop 112) is always upon the object-side focal surface of the second image-forming lens 113, and thus the optical system is kept telecentric. Thus, the phenomenon of a stereoscopic view that appears to become more concave or convex the nearer to the periphery of the screen despite actually being planar is eliminated. In addition, a lattice barrier 115 of a size such as that indicated in FIG. 10 is disposed near the front surface of the CCD for photography 116, so the eye fundus images passing through one aperture 112a of the photographic stop 112 are incident upon pixel columns R11 through R15 for the right eye for stereoscopic viewing at every other column, but are not incident upon pixel columns L11 through L15 for the left eye for stereoscopic viewing. Similarly, the eye fundus images passing through the other aperture 112b are incident upon pixel columns L11 through L15 for the left eye for stereoscopic viewing, but are not incident upon pixel columns R11 through R15 for the right eye for stereoscopic viewing, so there is no crosstalk between the left and right eye fundus images upon the CCD image pickup surface and good eye fundus images for stereoscopic viewing can be obtained.

Figure 13A:
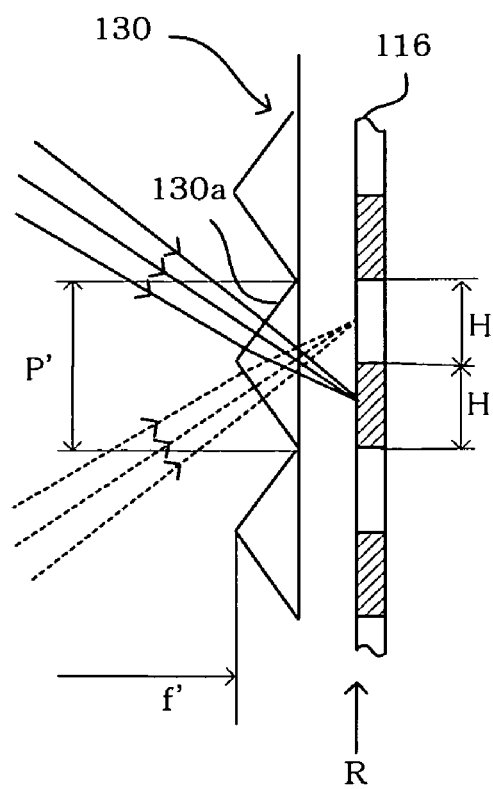
FIG. 13a is an illustrative view showing the layout of the lenticular prism in front of the CCD used for photography.
Figure 13B:
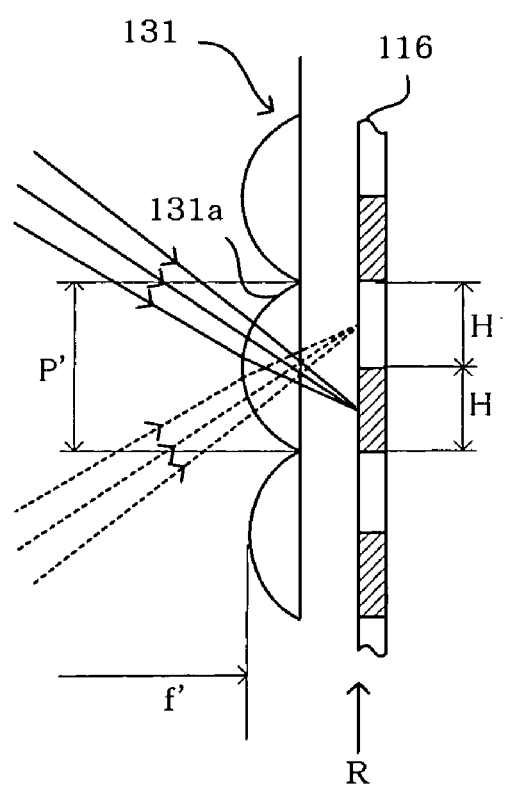
FIG. 13b is an illustrative view showing the layout of the lenticular lens in front of the CCD used for photography.

Note that the lattice barrier described above is an optical element comprising a lattice-type light-shading plate, but this can be replaced with a lenticular-type optical element, an example of which is shown in FIGS. 13a and 13b. FIG. 13a is one that uses a lenticular prism 130, being disposed such that the prism pitch (distance between prism vertices) P' is twice the pixel width H, and the vertices of each individual prism 130a are aligned with the boundaries between two adjacent pixels of the CCD for photography 116, and such that the vertices of the individual prisms 130a are positioned upon the image-side focal surface of the second image-forming lens 113.

In addition, FIG. 13b is one that uses a lenticular lens 131, being disposed such that the lens pitch (distance between lens vertices) P' is twice the pixel width H, and the vertices of each individual lens 131a are aligned with the boundaries between two adjacent pixels of the CCD for photography 116, and such that the vertices of the individual lenses 131a are positioned upon the image-side focal surface of the second image-forming lens 113. In either configuration, the eye fundus images passing through one aperture 112a of the photographic stop 112 are deflected at the prism surface or lens surface and thus formed upon pixel columns for the right eye for stereoscopic viewing (the shaded portions) at every other column, while the eye fundus images passing through the other aperture 112b are formed upon pixel columns for the left eye for stereoscopic viewing (the portions not shaded) at every other column, so the same meritorious effect as when using a lattice barrier is obtained.

Figure 12B:
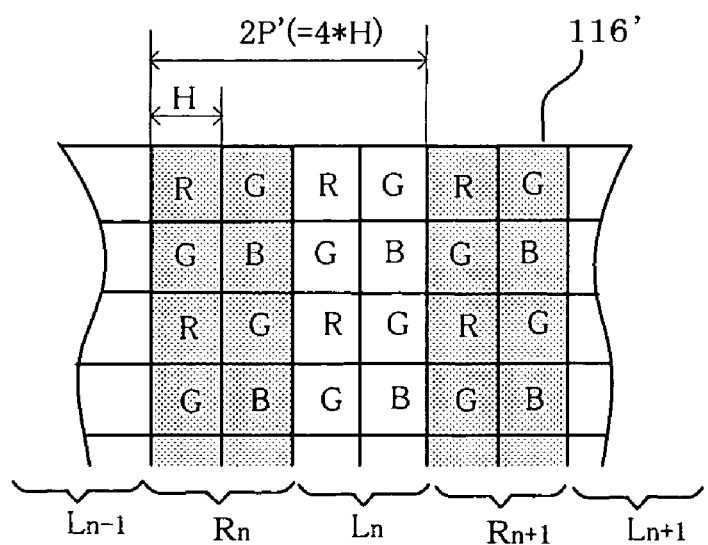
FIG. 12b is an illustrative view showing the layout of the pixel columns of a color CCD.

Note that when a single-chip color CCD is used as the image pickup means, individual pixels are typically made color sensitive by the use of a three-color filter as shown in FIG. 12b. When images for the right eye and for the left eye for stereoscopic viewing, respectively, are obtained with pixel columns at every other column as described above, the image for the left eye for stereoscopic viewing may consist of R and G pixels and the image for the right eye for stereoscopic viewing may consist of G and B pixels, so the left and right images for stereoscopic viewing may be differently colored. To solve this problem, as shown in FIG. 12b, the lattice barrier (or lenticular lens or lenticular prism) may be used to guide the eye fundus image from one aperture 112a of the photographic stop to two adjacent pixel columns (the portions indicated by shading) of a color CCD 116', and guide the eye fundus image from the other aperture 112b to two intervening pixel columns (the portions not shaded). To do this, when a lattice slit is used, the slit width is doubled (to 2*H) and the slit pitch is also doubled (to 4*H). In addition, when a lenticular prism or lenticular lens is used, the prism pitch or lens pitch is also doubled (to 4*H). By doing so, it is possible to obtain left and right images of the same color. Note that in FIG. 12b, the pixels that are shown as being R sensitive are assumed to be ones that also receive light in the infrared region.

In the above embodiment, the images picked up by the CCD for photography 116 may be displayed in stereo by a commercial lenticular-type monitor, parallax barrier-type monitor or other such display means, or it can be viewed stereoscopically using polarized glasses.

In addition, in the embodiment described above, the photographic stop 112 and the lattice barrier 115, lenticular prism 130 or lenticular lens 131 disposed in front of the CCD for photography 116 may also be detachably disposed upon the optical path. In this case, monocular photography may be performed by moving these elements out of the optical path. In this case, the photographic stop 112 is replaced with a one-aperture photographic stop and the slit 106 disposed in the illumination optical system is replaced with an illumination slit for monocular viewing.

What is claimed is:

1. An ophthalmic photography apparatus that includes an optical system for forming an image of the fundus of an eye being examined, and image pickup means that has a plurality of pixels in a matrix array disposed at the position where the image of the eye fundus is formed by the optical system, said ophthalmic photography apparatus comprising:

a lens movable within the optical system along the optical axis for compensation for shifts in the image-formation position due to differences in diopter of the eye being examined;

a stop with two apertures provided at a position substantially conjugate to the anterior ocular segment of the eye being examined; and a deflecting optical element provided near the imaging surface of the image pickup means;

wherein the exit pupil position of the optical system is set to be at infinity, and the image pickup means and the deflecting optical element are disposed such that the light that is incident upon one pixel column of the image pickup means via the optical deflecting element is only that light that passed through one of the two apertures of the stop and light from both apertures is incident upon alternate pixel columns of the image pickup means.

2. An ophthalmic photography apparatus that includes a first optical system for forming an image of the fundus of an eye being examined, a field stop disposed at a fundus-conjugate position in the first optical system, a second optical system for reforming the eye fundus image formed near the field stop, and image pickup means that has a plurality of pixels in a matrix array disposed at the position where the image of the eye fundus is formed by the second optical system, said ophthalmic photography apparatus comprising:

a lens movable within the first optical system along the optical axis for compensation for shifts in the image-formation position due to differences in diopter of the eye being examined;

a stop with two apertures disposed within the second optical system or in the vicinity thereof at a position substantially conjugate to the anterior ocular segment of the eye being examined; and a deflecting optical element provided near the imaging surface of the image pickup means;

wherein the exit pupil position of the second optical system is set to be at infinity, and the image pickup means and the deflecting optical element are disposed such that the light that is incident upon one pixel column of the image pickup means via the deflecting optical element is only that light that passed through one of the two apertures of the stop, and light from both apertures is incident upon alternate pixel columns of the image pickup means.

3. An ophthalmic photography apparatus according to claim 2, wherein an optical path dividing means is disposed between the field stop and the image pickup means to provide an divided optical path on which another image pickup means is disposed.

4. An ophthalmic photography apparatus according to claim 3, wherein a ring slit provided in the illumination optical system and a stop substantially conjugate to the anterior ocular segment disposed within the first optical system or in the vicinity thereof are changeable depending on the selection of both the image pickup means.

5. An ophthalmic photography apparatus that uses an electronic image pickup means disposed at a position conjugate to the fundus of an eye being examined, said ophthalmic photography apparatus comprising:
  an objective lens that forms an image of light reflected from the fundus of an eye being examined;
  a first image-forming lens disposed behind said objective lens;
  a photographic stop disposed on the image-side focal surface of the first image-forming lens;
  a second image-forming lens disposed such that its object-side focal surface coincides with the position of the photographic stop;
  an optical element disposed on the image-side focal surface of the second image-forming lens for guiding the eye fundus image to the electronic image pickup means; and
  drive means for moving the first image-forming lens, photographic stop, second image-forming lens, optical element and electronic image pickup means as a unit along the optical axis;
  wherein the object-side focal surface of the objective lens is brought into coincidence with the anterior ocular segment of the eye being examined, and the first image-forming lens, photographic stop, second image-forming lens, optical element and electronic image pickup means are moved as a unit along the optical axis for focus adjustment.

6. An ophthalmic photography apparatus according to claim 5, wherein the photographic stop is a stop provided with two apertures, and the optical element guides the eye fundus images from one of the apertures of the photographic stop to pixel columns of the electronic image pickup means at every other column and guides the eye fundus images from the other of the apertures of the photographic stop to pixel columns interspersed between the pixel columns at every other column.

7. An ophthalmic photography apparatus according to claim 5, wherein the photographic stop is a stop provided with two apertures, and the optical element guides the eye fundus images from one of the apertures of the photographic stop to two adjacent pixel columns of the electronic image pickup means at every other set of two columns and guides the eye fundus images from the other of the apertures of the photographic stop to two adjacent pixel columns interspersed between the two pixel columns at every other set of two columns.

8. An ophthalmic photography apparatus according to claim 5, wherein a photographic mask is disposed at a position conjugate to the eye fundus in front of the first image-forming lens to determine the range of the eye fundus to be photographed.

9. An ophthalmic photography apparatus according to claim 8, wherein the photographic mask is linked to and moved by the drive means.

10. An ophthalmic photography apparatus according to claim 5, wherein the photographic stop and the optical element are removably provided in the optical path.

11. An ophthalmic photography apparatus according to claim 5, wherein the optical element is a lattice-type light-shading plate provided with a plurality of slit-shaped apertures.

12. An ophthalmic photography apparatus according to claim 5, wherein the optical element is a lenticular-type optical element.

* * * * *